United States Patent
Ogawa

(10) Patent No.: US 10,723,689 B2
(45) Date of Patent: Jul. 28, 2020

(54) PRODUCTION METHOD FOR (METH)ACRYLIC ACID OR ESTER THEREOF

(71) Applicant: Mitsubishi Chemical Corporation, Chiyoda-ku (JP)

(72) Inventor: Yasushi Ogawa, Mie (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/233,308

(22) Filed: Dec. 27, 2018

(65) Prior Publication Data

US 2019/0127308 A1    May 2, 2019

Related U.S. Application Data

(63) Continuation of application No. PCT/JP2017/009724, filed on Mar. 10, 2017.

(30) Foreign Application Priority Data

Jun. 29, 2016  (JP) .................................. 2016-128861

(51) Int. Cl.
*C07C 51/44* (2006.01)
*F28F 9/22* (2006.01)
(Continued)

(52) U.S. Cl.
CPC ............ *C07C 51/44* (2013.01); *B01D 3/007* (2013.01); *B01D 3/14* (2013.01); *C07C 57/04* (2013.01);
(Continued)

(58) Field of Classification Search
CPC ......... C07C 51/44; C07C 51/04; C07C 67/54; C07C 69/54
(Continued)

(56) References Cited

U.S. PATENT DOCUMENTS 4,365,081 A    12/1982 Shimizu et al.
4,369,097 A    1/1983 Nezu et al.
(Continued)

FOREIGN PATENT DOCUMENTS

EP    1 748 037 A1    1/2007
JP    60-43056 B2    9/1985
(Continued)

OTHER PUBLICATIONS

International Search Report dated Jun. 13, 2017 in PCT/JP2017/009724 (with English translation), 5 pages.
(Continued)

*Primary Examiner* — Deborah D Carr
(74) *Attorney, Agent, or Firm* — Oblon, McClelland, Maier & Neustadt, L.L.P.

(57) ABSTRACT

Using a vertical multi-tube heat exchanger which includes a tubular body, an upper tube plate and a lower tube plate, a plurality of heat transfer tubes, and lid sections and in which the distillation gas introduced into a receiving chamber is cooled in the course of passing through the heat transfer tube and turns into a condensate, a solution containing polymerization inhibitor is introduced into the receiving chamber. Some of the plurality of heat transfer tubes have an upper end protruding above the upper tube plate, with the remainings being not protruding, and the solution containing polymerization inhibitor coming into contact with the distillation gas in the receiving chamber forms a liquid flow layer with a predetermined liquid depth on the upper tube plate.

4 Claims, 4 Drawing Sheets

(51) Int. Cl.
  *F28D 7/16* (2006.01)
  *F28F 19/00* (2006.01)
  *B01D 3/00* (2006.01)
  *B01D 3/14* (2006.01)
  *C07C 57/04* (2006.01)
  *C07C 67/54* (2006.01)
  *C07C 69/54* (2006.01)

(52) U.S. Cl.
  CPC .............. *C07C 67/54* (2013.01); *C07C 69/54* (2013.01); *F28D 7/16* (2013.01); *F28F 9/22* (2013.01); *F28F 19/00* (2013.01)

(58) Field of Classification Search
  USPC ........................................................ 560/218
  See application file for complete search history.

(56) References Cited

U.S. PATENT DOCUMENTS

| | | | |
|---|---|---|---|
| 6,620,969 | B1 | 9/2003 | Nishimura et al. |
| 2001/0017202 | A1 | 8/2001 | Mitsumoto et al. |
| 2003/0111216 | A1 | 6/2003 | Hirao et al. |
| 2005/0040023 | A1 | 2/2005 | Hino et al. |

FOREIGN PATENT DOCUMENTS

| | | | | |
|---|---|---|---|---|
| JP | 63-11921 | B2 | | 3/1988 |
| JP | 2000-254484 | A | | 9/2000 |
| JP | 2000-344688 | A | | 12/2000 |
| JP | 2000344688 | A | * | 12/2000 |
| JP | 2001-241883 | A | | 9/2001 |
| JP | 2001241883 | A | * | 9/2001 ........... F28D 7/1607 |
| JP | 2003-240479 | A | | 8/2003 |
| JP | 2003-240482 | A | | 8/2003 |
| JP | 2003240482 | A | * | 8/2003 |
| JP | 6311921 | B2 | * | 4/2018 |
| RU | 2 372 130 | C9 | | 8/2007 |

OTHER PUBLICATIONS

Written Opinion of the International Searching Authority dated Jun. 13, 2017 in PCT/JP2017/009724 filed Mar. 10, 2017 (with English translation ), 11 pages.

"Shell and Tube Heat Exchangers" JIS B 8249, Japanese Industrial Standards, 1999, 36 pages, (Partial English translation).

Extended European Search Report dated Jun. 3, 2019 in Patent Application No. 17819556.6, 7 pages.

Combined Russian Office Action and Search Report dated Aug. 30, 2019 in Russian Patent Application No. 2018146863 (with English translation), 12 pages.

Iranian Office Action dated Sep. 16, 2019 in Iranian Patent Application No. 139750140003008477 (with English translation), 9 pages.

Office Action dated Feb. 24, 2020 in Indian Patent Application No. 201817049288 filed Dec. 27, 2018 with English translation, 6 pages.

* cited by examiner

PRODUCTION METHOD FOR (METH)ACRYLIC ACID OR ESTER THEREOF

TECHNICAL FIELD

The present invention relates to a production method of a (meth)acrylic acid or an ester thereof (hereinafter, sometimes referred to as "(meth)acrylic acids"). More specifically, the present invention relates to a production method of (meth)acrylic acids, including a step of forming a distillation gas in a distillation column from a process liquid containing (meth)acrylic acids and allowing the distillation gas to turn into a condensate through a vertical multi-tube heat exchanger, wherein continuous production of (meth)acrylic acids is stably performed for a long period of time while preventing production and accumulation of a polymerization product in the vertical multi-tube heat exchanger.

In this connection, the (meth)acrylic acid as used in the present description is a collective term for an acrylic acid and a methacrylic acid and may be either one or both thereof. In addition, the (meth)acrylic acids may be either one of a (meth)acrylic acid and a (meth)acrylic acid ester or may contain both.

BACKGROUND ART

The (meth)acrylic acids are a compound easy to polymerize, and the polymerization is promoted in particular under high temperature conditions. If the (meth)acrylic acids are polymerized in the production process thereof, the apparatus/piping equipment are clogged by a solid matter produced by the polymerization and in an extreme case, the operation cannot be continued. In addition, even if shutdown due to clogging of the apparatus/piping equipment is avoided, there arise many problems, for example, an increase in the cleaning frequency of the apparatus/piping equipment during normal operation or in the cleaning load at the time of periodic maintenance.

To cope with these problems, when distilling (meth) acrylic acids, a polymerization inhibitor is added so as to prevent the polymerization thereof. However, many polymerization inhibitors have a low vapor pressure compared with (meth)acrylic acids, and the polymerization inhibitor added is often scarcely contained in the gas of volatilized (meth)acrylic acids. Even though the polymerization inhibitor is not contained, as the density of (meth)acrylic acids in a gas state is low, it is expected that a polymerization reaction does not substantially occur. However, when the gas is once condensed and turns into a condensate, the condensate has high polymerizability and brings about clogging, etc. of the apparatus. The apparatus in which the state above is most likely produced is a condenser for cooling and condensing a distillate gas from a heating distillation apparatus. Accordingly, various studies are being made so as to prevent (meth)acrylic acids from polymerization in the condenser.

For example, Patent Document 1 describes a method for distilling and purifying 2-hydroxy (meth)acrylate, wherein a vapor of 2-hydroxy (meth)acrylate is turned into a condensate in a direct contact-type condenser, part of the obtained condensate is further cooled, the cooled condensate is fed as a spray solution into the direct contact-type condenser so as to swiftly lower the temperature of the vapor of 2-hydroxy (meth)acrylate, and a polymerization inhibitor is added to the spray solution, thereby suppressing generation of a polymerization product in the condenser.

In Patent Document 2, for distilling and purifying an easily polymerizable compound, when a vapor of an easily polymerizable compound is cooled in a condenser and turned into a condensate, with use of a vertical multi-tube heat exchanger as the condenser, part of the obtained condensate is circulated to the gas introduction side of the vertical multi-tube heat exchanger and uniformly sprayed on the upper tube plate to wet the inner surface of a condenser tube (heat transfer tube) with the condensate flowing down inside the tube, thereby preventing a distillate gas in an overheated state from coming into direct contact with the condenser tube to produce a polymerization product. In Patent Document 2, it is stated that a polymerization inhibitor may be added to the condensate circulated.

In this connection, as stated in Non-Patent Document 1, in a vertical multi-tube heat exchanger, for construction reasons, it is a common practice to slightly protrude a heat transfer tube end from a tube plate surface at the time of fixing the heat transfer tube to the tube plate. Accordingly, in the vertical multi-tube heat exchanger described in Patent Document 2, it is thought that upper ends of all heat transfer tubes protrude from the upper tube plate surface.

On the other hand, Patent Document 3 demonstrates that compared with a case where a multi-tube heat exchanger having a heat transfer tube protruded by 1 mm on average from a tube plate surface is used as the vertical multi-tube heat exchanger for cooling and condensing a gas of an easily polymerizable compound, use of a multi-tube heat exchanger having a heat transfer tube which is not protruded from a tube plate surface makes it possible to suppress accumulation of a polymerization product inside the multi-tube heat exchanger. In Patent Document 3, it is stated that the heat transfer tube is not protruded from the upper tube plate and a process fluid can thereby be prevented from staying on the upper tube plate surface, as a result, polymerization of an easily polymerizable compound can be suppressed.

In Patent Document 4, as a multi-tube heat exchanger with ensuring sufficient strength at the junction between the heat transfer tube and the upper tube plate, which suppresses production of a polymerization product on an upper tube plate surface as well as inside a heat transfer tube, thereby getting rid of damage to the heat exchanger, and which enables continuous operation for a long period of time, a multi-tube heat exchanger wherein out of a plurality of heat transfer tubes, some are a heat transfer tube having an upper end which is not protruded from the upper tube plate and others are a heat transfer tube having an upper end protruded from the upper tube plate is described.

RELATED ART

Patent Document

Patent Document 1: JP-B-S60-43056
Patent Document 2: JP-B-S63-11921
Patent Document 3: JP-A-2000-254484
Patent Document 4: JP-A-2003-240482

Non-Patent Document

Non-Patent Document 1: Japanese Industrial Standards JIS-B8249 (1999)

SUMMARY OF THE INVENTION

Problems that the Invention is to Solve

However, all of these conventional techniques are not fully satisfied as described below.

The method of Patent Document 1 requires a spray solution of several times to several score times, in terms of weight ratio, relative to the vapor that is a fluid to be condensed. Accordingly, the equipment necessary for cooling or circulating a condensate utilized as a spray solution and forming a spray solution is enlarged, and this is disadvantageous from an economical aspect, among others, in a large-scale equipment.

The method of Patent Document 2 is one of techniques widely known in industry and is advantageous compared with the method of Patent Document 1 in that the amount of condensate circulated and sprayed is merely from 1/10 to 1 times at most relative to the vapor as a fluid to be condensed. However, when the temperature of the vapor as a fluid to be condensed is high, the polymerization preventing effect is insufficient. Thus, further improvements are demanded in terms of the polymerization preventing effect.

Also in the case of using a vertical multi-tube heat exchanger described in Patent Document 3, in which all heat transfer tubes are not protruded from the upper tube plate, and condensing a distillate gas while circulating and spraying a condensate as described in Patent Document 2, if the temperature of a vapor as a fluid to be condensed is high, production of a polymerization product is still unavoidable.

Although Patent Document 4 describes a multi-tube heat exchanger in which some heat transfer tubes do not protrude from the upper tube plate and others are protruded from the upper tube plate, introduction of a solution containing polymerization inhibitor into a receiving chamber is neither described not suggested in Patent Document 4. Patent Document 4 is an invention based on not storing a solution on the upper tube plate (paragraph [0043], etc. of Patent Document 4), and its technical idea is contradictory with forming of a liquid flow layer (a layer having a liquid depth, in which the liquid is renewed without delay) according to the present invention.

In addition, the conditions of Patent Document 4 hold a possibility of occurrence of drift of the distillate gas, and although a region getting wet or dry is generated over time on the upper tube plate due to drift of the distillate gas, getting wet indicates the liquid is not flowing but staying, making it impossible to avoid production of polymerization.

An object of the present invention is to solve the above-described conventional problems and provide a production method of (meth)acrylic acids, including a step of forming a distillation gas in a distillation column from a process liquid containing (meth)acrylic acids and allowing the distillation gas to turn into a condensate through a vertical multi-tube heat exchanger, wherein continuous production of (meth)acrylic acids can be stably performed for a long period of time while preventing production and accumulation of a polymerization product in the vertical multi-tube heat exchanger.

Means for Solving the Problems

As a result of many intensive studies to attain the object above, the present inventors have found that when a vertical multi-tube heat exchanger having a specific configuration is used as the vertical multi-tube heat exchanger for condensing a distillation gas such as (meth)acrylic acids and after brining the distillation gas into contact with a solution containing polymerization inhibitor inside a receiving chamber of the vertical multi-tube heat exchanger, a liquid flow layer having a predetermined liquid depth is caused to be formed on the upper tube plate and caused to flow down a heat transfer tube, continuous production of (meth)acrylic acids can be stably performed for a long period of time while suppressing production and accumulation of a polymerization product.

The present invention has been achieved based on this finding, and the gist thereof resides in the following.

[1] A production method of a (meth)acrylic acid or an ester thereof, comprising a step of forming a distillation gas in a distillation column from a process liquid containing a (meth)acrylic acid or an ester thereof and allowing the distillation gas to turn into a condensate through a vertical multi-tube heat exchanger, wherein a vertical multi-tube heat exchanger is used containing:

a tubular body, an upper tube plate and a lower tube plate arranged respectively on the upper end side and the lower end side of the tubular body, a plurality of heat transfer tubes erected between the upper tube plate and the lower tube plate, and lid sections arranged respectively on the upper side of the upper tube plate and on the lower side of the lower tube plate, and in which the distillation gas introduced into a receiving chamber formed by the upper tube plate and the lid section on the upper side of the upper tube plate is cooled in the course of passing through the heat transfer tube and turns into a condensate, a solution containing polymerization inhibitor is introduced into the receiving chamber, and the solution containing polymerization inhibitor coming into contact with the distillation gas in the receiving chamber forms a liquid flow layer on the upper tube plate and then flows down inside the heat transfer tube.

[2] The production method of a (meth)acrylic acid or an ester thereof according to [1], wherein the liquid depth of the liquid flow layer is 2 mm or more.

[3] A production method of a (meth)acrylic acid or an ester thereof, comprising a step of forming a distillation gas in a distillation column from a process liquid containing a (meth)acrylic acid or an ester thereof and allowing the distillation gas to turn into a condensate through a vertical multi-tube heat exchanger, wherein a vertical multi-tube heat exchanger is used containing:

a tubular body, an upper tube plate and a lower tube plate arranged respectively on the upper end side and the lower end side of the tubular body, a plurality of heat transfer tubes erected between the upper tube plate and the lower tube plate, and lid sections arranged respectively on the upper side of the upper tube plate and on the lower side of the lower tube plate, and in which some of the plurality of heat transfer tubes have an upper end protruding above the upper tube plate, with the remainings being not protruding, and the distillation gas introduced into a receiving chamber formed by the upper tube plate and the lid section on the upper side of the upper tube plate is cooled in the course of passing through the heat transfer tube and turns into a condensate, a solution containing polymerization inhibitor is introduced into the receiving chamber, and the solution containing polymerization inhibitor coming into contact with the distillation gas in the receiving chamber flows down inside the non-protruding heat transfer tube from the upper tube plate.

[4] The production method of a (meth)acrylic acid or an ester thereof according to any one of [1] to [3], wherein the solution containing polymerization inhibitor contains the condensate.

Effect of the Invention

According to the present invention, in a production method of (meth)acrylic acids, including a step of forming a distillation gas in a distillation column from a process liquid containing (meth)acrylic acids and allowing the distillation gas to turn into a condensate through a vertical multi-tube heat exchanger, continuous production of (meth) acrylic acids can be stably performed for a long period of time while preventing production and accumulation of a polymerization product in the vertical multi-tube heat exchanger.

MODE FOR CARRYING OUT THE INVENTION

Figure 1:
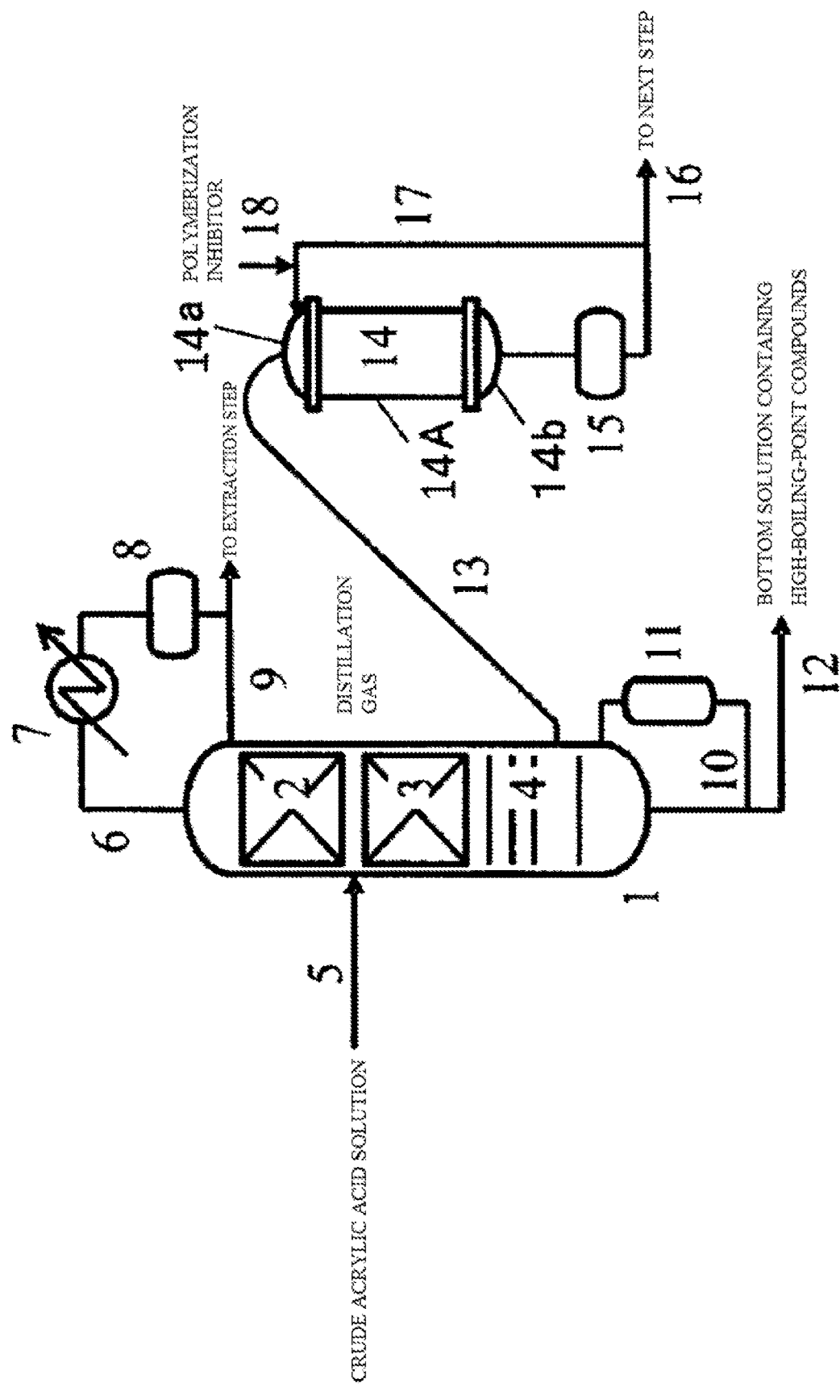
FIG. 1 is a schematic system diagram illustrating one example of the embodiment of the production method of (meth)acrylic acids according to the present invention.

Although the embodiments of the production method of (meth)acrylic acids of the present invention are described in detail below by referring to the drawings, the present invention is not limited to the contents in the following description and can be implemented by making various changes within the scope of the gist of the present invention.

In the following, although an embodiment of distilling an acrylic acid as the (meth)acrylic acids and condensing the distillation gas is described, the present invention is not limited to an acrylic acid and can be widely applied to distillation and condensation of (meth)acrylic acids.

Furthermore, in the following, the numerical values provided to the dimension of each section of the vertical multi-tube heat exchanger are exemplary only as a vertical multi-tube heat exchanger used in general-purpose commercial facilities, and the dimension of each section of the vertical multi-tube heat exchanger according to the present invention is not limited by any means to those described below.

Figure 2:
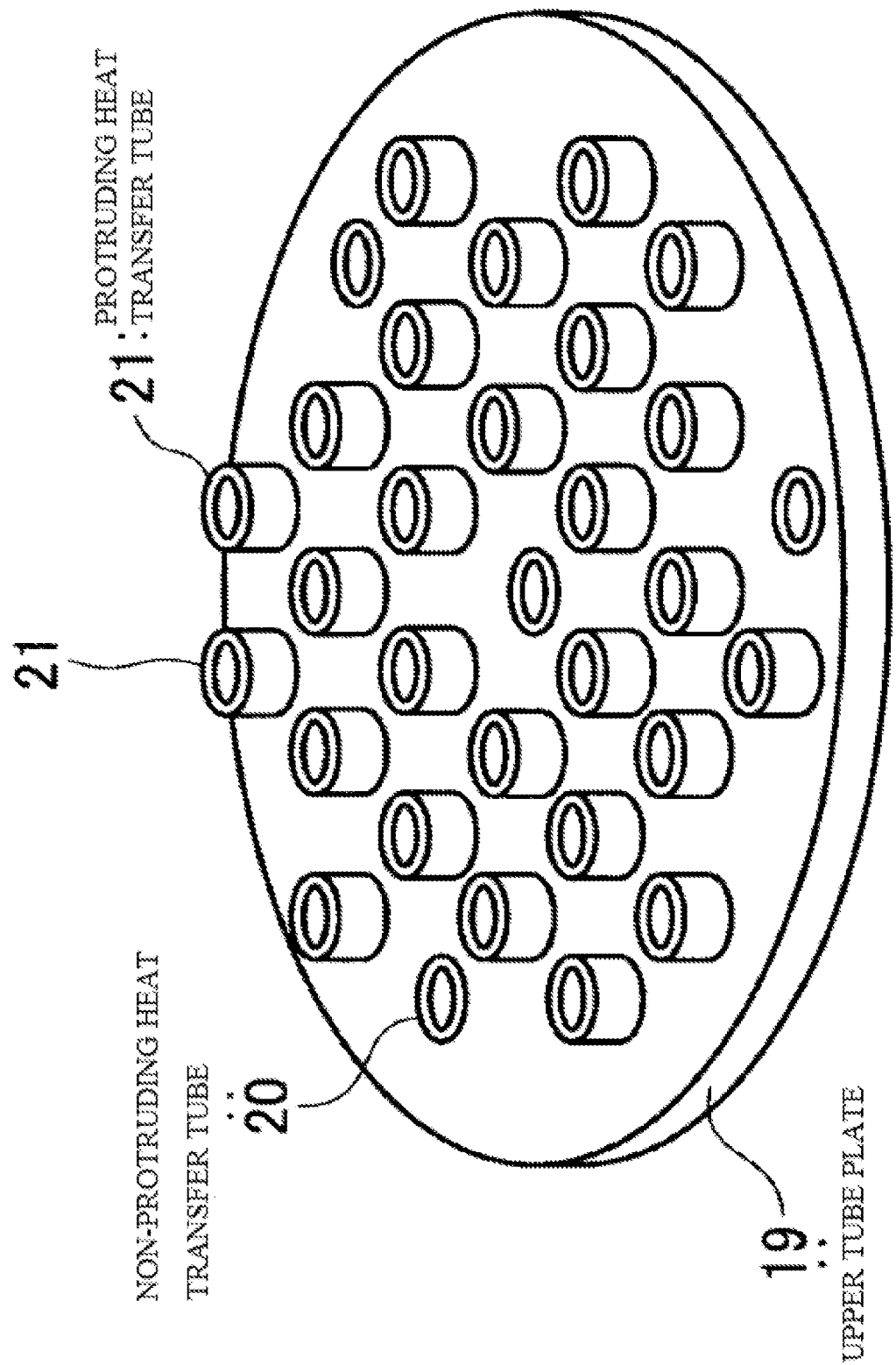
FIG. 2 is a perspective diagram of the upper tube plate surface of the vertical multi-tube heat exchanger of FIG. 1.

FIG. 1 is a schematic system diagram illustrating one example of the embodiment of the production method of (meth)acrylic acids according to the present invention, and FIG. 2 is a perspective diagram of the upper tube plate surface of the vertical multi-tube heat exchanger of FIG. 1.

The present invention is effective particularly when the gas flowing in the vertical multi-tube heat exchanger is at a high temperature, and therefore, FIG. 1 illustrates a case where a high-temperature distillation gas from a distillation column is directly introduced into the vertical multi-tube heat exchanger and condensed. However, the present invention is not limited to such an embodiment and can also be applied, for example, to an embodiment where a relatively low-temperature uncondensed gas after partially condensing a high-temperature distillation gas from a distillation column by a heat exchanger (condenser) provided in a stage prior to the vertical multi-tube heat exchanger is further condensed by the vertical multi-tube heat exchanger.

FIG. 1 illustrates, in the production process of an acrylic acid, a step of separating by distillation an extraction solvent, an acrylic acid and a high-boiling-point impurity from an acrylic acid-containing solution (crude acrylic acid solution) which is solvent-extracted from a reaction product solution of acrylic acid. In FIG. 1, (1) is a distillation column including, as inserts, a regular filler (2) in the enriching section, an irregular filler (3) in the upper collection section, and plates (4) formed of a weirless perforated plate disposed below the fillers. A crude acrylic acid solution containing an extraction solvent is fed to the distillation column (1) by a feed line (5). An extraction solvent vapor separated by a top gas line (6) is cooled and condensed by a plate heat exchanger (7) and collected in a reflux tank (8). Part of the recovered extraction solvent is circulated to the top section of the distillation column (1) by a reflux line (9), and the remaining is sent to an extraction step (not illustrated). The bottom solution of the distillation column (1) is heated in a reboiler (11) after passing through a circulation line (10) and then circulated to the distillation column (1). Part of the bottom solution containing high-boiling-point compounds is recovered from a withdrawal line (12).

A fluid containing an acrylic acid as the main component is withdrawn in a gas state from a middle withdrawal line (13) provided on a lower side of the distillation column (1), and the withdrawn distillation gas is fed to a vertical multi-tube heat exchanger (14). The outer periphery of the middle withdrawal line (13) is heated by an electric heater or a vapor piping and further kept warm with a heat-insulating material so as to prevent the withdrawn distillation gas from condensing halfway. In addition, the middle withdrawal line (13) is downwardly inclined toward the distillation column (1) side so that even if a condensate is produced, the condensate cannot stay inside.

The temperature of the distillation gas fed to the vertical multi-tube heat exchanger is usually on the order of 50 to 110° C. However, as described above, when the distillation gas is partially condensed by a heat exchanger (condenser) provided in a stage prior to the vertical multi-tube heat exchanger, the temperature of the uncondensed gas fed to the vertical multi-tube heat exchanger is approximately from 15 to 50° C.

The vertical multi-tube heat exchanger (14) has a tubular body (14A) and lid sections (14*a*) and (14*b*) provided at both ends thereof and has a plurality of heat transfer tubes (not illustrated) inside the tubular body (14A).

More specifically, the vertical multi-tube heat exchanger (14) has a tubular body (14A) disposed such that the axial direction runs in the vertical direction, an upper tube plate and a lower tube plate (both not illustrated) arranged respectively on the upper end side and the lower end side of the tubular body (14A) such that the plate surface runs in the horizontal direction, a plurality of heat transfer tubes (not illustrated) erected in the vertical direction between the upper tube plate and the lower tube plate by fixing respective tube end parts to the upper tube plate and the lower tube plate, and domed lid sections (14*a*) and (14*b*) arranged respectively on the upper side of the upper tube plate and on the lower side of the lower tube plate, and a distillation gas containing an acrylic acid as the main component from the middle withdrawal line (13) is introduced into a receiving chamber (not illustrated) formed in a space between the upper tube plate and the lid section (14*a*) of the vertical multi-tube heat exchanger (14).

An inflow port (not illustrated) for a cooling medium (cooling water) is provided in the lower part of the side surface between the upper tube plate and the lower tube plate of the tubular body (14A), an outflow port (not illustrated) for the cooling medium is provided in the upper part, and the distillation gas introduced into the receiving chamber of the vertical multi-tube heat exchanger (14) is cooled and condensed in the course of flowing down inside the heat transfer tube by the cooling medium flowing outside the heat transfer tube, recovered as a crude acrylic acid in a drum (15) through a take-out chamber (not illustrated) formed in a space between the lower tube plate and the lid section (14b), and sent to the next step by a line (16) to next step. Part of the crude acrylic acid is circulated to the receiving chamber side of the vertical multi-tube heat exchanger (14) by a circulation line (17). A solution containing a polymerization inhibitor is fed to the circulation line (17) through a polymerization inhibitor feed line (18).

Although the form of feed of a crude acrylic acid circulating liquid containing a polymerization inhibitor (solution containing polymerization inhibitor) to the receiving chamber is not particularly limited, in order to bring the crude acrylic acid circulating liquid into full contact with the distillation gas introduced into the receiving chamber, that is, in order to increase the contact area of the crude acrylic acid circulating liquid with the distillation gas as much as possible, and to spread the crude acrylic acid circulating liquid all over the upper tube plate, the crude acrylic acid circulating liquid is preferably sprayed like mist throughout the interior of the receiving chamber from an atomizing nozzle provided in the upper lid section (14a).

FIG. 2 is a perspective diagram of the upper tube plate surface in the vertical multi-tube heat exchanger (14) of FIG. 1. Upper end parts of heat transfer tubes are fixed at regular intervals to the tope surface of the upper tube plate (19). Some heat transfer tubes (21) have a tube end protruded to the same height from the upper tube plate (19) surface (hereinafter, the heat transfer tube protruded is sometimes referred to as "protruding heat transfer tube"). On the other hand, the heat transfer tubes (20) other than the protruding heat transfer tubes (21) have a tube end which is not protruded from the upper tube plate (19) surface and are fixed substantially flush with the top surface of the upper tube plate (19) (hereinafter, the heat transfer tube having a tube end which is not protruded from the upper tube plate is sometimes referred to as "non-protruding heat transfer tube").

In the present invention, a vertical multi-tube heat exchanger (14) thus configured to protrude upper ends of some heat transfer tubes (21) above the upper tube plate (19) and not to protrude upper ends of other heat transfer tubes (20) from the upper tube plate (19) surface is used, so that generation and accumulation of a polymerization product of an acrylic acid inside the vertical multi-tube heat exchanger can be suppressed and stable operation can thereby be continued.

Details on the mechanism of action thereof are not clarified, but the mechanism is presumed as follows.

When the crude acrylic acid circulating liquid introduced into the receiving chamber is put into contact with the distillation gas, part of the distillation gas is condensed due to contact with the crude acrylic acid circulating liquid, and the residue still in a gas state reaches the upper tube plate in a mixed state with the crude acrylic acid circulating liquid. At this time, a part flows into the protruding heat transfer tube and after flowing down inside the heat transfer tube, turns into a condensate, and the residue forms a gas-containing liquid pool having a liquid depth according to the protrusion height of the protruding heat transfer tube.

However, since the upper end is not protruded from the upper tube plate in the remainings of the heat transfer tubes, the gas-containing liquid forming a pool on the upper tube plate moves on the upper tube plate toward the non-protruding heat transfer tube side and after flowing down inside the non-protruding heat transfer tube, turns into a condensate.

It is considered that since the crude acrylic acid circulating liquid containing a polymerization inhibitor thus always maintains a predetermined liquid depth on the top surface of the upper tube plate in the state containing a distillation gas or a condensate thereof and at the same time, moves on the upper tube plate to flow in and flow down the non-protruding heat transfer tube, the liquid on the upper tube plate forms a liquid flow layer that is renewed without delay, and polymerization of an acrylic acid in the distillation gas is thereby suppressed.

More specifically, the "liquid flow layer" as used in the present invention is a "layer having a liquid depth formed on the upper tube plate, in which the liquid is renewed without delay".

According to the present invention, the distillation gas introduced into the receiving chamber is partially condensed by the crude acrylic acid circulating liquid containing a polymerization inhibitor and further partially condensed in the course of flowing as a liquid flow layer on the upper tube plate in the form of a mixed fluid with the crude acrylic acid circulating liquid containing a polymerization inhibitor and flowing into a heat transfer tube, and since the temperature drops to a certain extent and moreover, the liquid has become a mixed fluid fully mixed with the crude acrylic acid circulating liquid containing a polymerization inhibitor at the time of being cooled as it flows down the heat transfer tube, the polymerization preventing effect of the polymerization inhibitor is efficiently exerted, as a result, production and accumulation of a polymerization product are suppressed.

In contrast, in the general vertical multi-tube heat exchanger used in Patent Document 2, upper ends of all heat transfer tubes are protruding above the upper tube plate. Therefore, even if a liquid pool of the crude acrylic acid circulating liquid containing a polymerization inhibitor is formed, the liquid can hardly flow down the heat transfer tube together with the distillation gas, that is, the liquid pool is not renewed, and even when the crude acrylic acid circulating liquid containing a polymerization inhibitor is circulated, the polymerization preventing effect due to the circulation cannot be sufficiently obtained.

On the other hand, when all heat transfer tubes are configured not to protrude from the upper tube plate as in Patent Document 3, a liquid pool is not formed on the upper tube plate, making it impossible for the distillation gas and the crude acrylic acid circulating liquid containing a polymerization inhibitor to flow down inside the heat transfer tube in a uniformly mixed state, and after all, even when the crude acrylic acid circulating liquid containing a polymerization inhibitor is circulated, the polymerization preventing effect due to the circulation cannot be sufficiently obtained.

In the present invention, in order to unfailingly maintain a predetermined liquid depth on the entire upper tube plate surface, the protrusion height of the protruding heat transfer tube protruded above the upper tube plate is preferably 2 mm or more, and more preferably 3 mm or more. When the protrusion height of the protruding heat transfer tube is 2 mm or more, a liquid flow layer having a predetermined liquid depth is easily formed without being affected by the horizontal error of the heat exchanger disposed, the surface tension of the condensate, and the drift of the distillation gas introduced, etc. From the viewpoint of maintaining the liquid depth, the protrusion height of the protruding heat transfer tube is preferably higher, but if the height is excessively high, the liquid is hardly renewed, and therefore, the protrusion height is preferably 20 mm or less, more preferably 15 mm or less.

As to the protrusion height of the protruding heat transfer tube, it is preferred that the protruding heat transfer tubes all have substantially the same protrusion height. Here, substantially the same protrusion height means to have a deviation within the range which does not affect the holding of a uniform liquid flow layer on the upper tube plate. Specifically, the deviation is preferably within the range of ±2 mm relative to the preset protrusion height. However, when the preset protrusion height is less than 4 mm, the deviation is preferably within the range of ±1 mm of the preset protrusion height.

In addition, if the ratio of non-protruding heat transfer tubes to the total number of heat transfer tubes is large and the ratio of protruding heat transfer tubes is small, the liquid depth on the upper tube plate can hardly be maintained. On the contrary, if the ratio of non-protruding heat transfer tubes is small and the ratio of protruding heat transfer tubes is large, the liquid depth may be easily maintained, but the liquid flow on the upper tube plate is likely to be biased. Accordingly, the ratio of non-protruding heat transfer tubes is preferably 0.1% or more and 20% or less, relative to all heat transfer tubes. Furthermore, in order to form a uniform liquid flow layer on the upper tube plate, the non-protruding heat transfer tubes are preferably provided in a symmetric even arrangement on the upper tube plate surface. In the case where the total number of all heat transfer tubes is small, the non-protruding heat transfer tubes may be provided only in the central part on the upper tube plate, but it is more preferable to provide the non-protruding heat transfer tube also in the outer circumferential part or near the outer circumferential part of the upper tube plate. The number of non-protruding heat transfer tubes is preferably 3 or more, more preferably 4 or more. In the case of increasing the number of non-protruding heat transfer tubes along with increase in the total number of heat transfer tubes, they are preferably arranged in high symmetry with an equal distance between the mutual heat transfer tubes.

Although it may vary depending on the scale of the vertical multi-tube heat exchanger, usually, the area of the upper tube plate is approximately from 0.2 to 7 m$^2$ (diameter: approximately from 0.5 to 3 m), and the inside diameter of the heat transfer tube is approximately from 15 to 40 cm. The heat transfer tube is usually provided in an even arrangement at a density of 100 to 400 tubes/m$^2$ per area of the upper tube plate and therefore, in the present invention, it is preferred that from 0.1 to 20%, particularly from 0.1 to 5%, of these transfer tubes are a non-protruding heat transfer tube, with the arrangement thereof being an even arrangement on the upper tube plate, and others are a protruding heat transfer tube protruded by approximately from 2 to 20 mm, in particular, approximately from 3 to 15 mm, above the upper tube plate.

The polymerization preventing effect of the present invention is attributable to forming, on the upper tube plate, a liquid flow layer having a predetermined liquid depth, i.e., of usually 2 mm or more, preferably from 2 to 20 mm, more preferably from 3 to 15 mm, which moves on the upper tube plate and then flows in and flows down the heat transfer tube as described above. Accordingly, the means for polymerization prevention is not limited to the technique above of configuring some heat transfer tubes as a non-protruding heat transfer tube, but as long as such a liquid flow layer can be formed, any other means may be employed.

For example, the vertical multi-tube heat exchanger may also be designed such that the heat transfer tubes all are a non-protruding heat transfer tube and a projection serving as a weir is formed between non-protruding heat transfer tubes, thereby maintaining the liquid depth of the liquid flow layer.

The present invention can be conducted in the same manner as conventional methods except that a liquid flow layer having a predetermined liquid depth is formed on the upper tube plate, for example, by designing the protrusion height of the heat transfer tube on the upper tube plate as described above. Additionally, regarding the configuration of the vertical multi-tube heat exchanger, the same as those of conventional vertical multi-tube heat exchangers may be employed except for the protruding or non-protruding design of heat transfer tubes on the upper tube plate.

Out of the condensate withdrawn from the lower part of the vertical multi-tube heat exchange, the amount of the crude acrylic acid circulating liquid circulated to the receiving chamber is, in view of the polymerization preventing effect due to circulation of the crude acrylic acid circulating liquid and the production efficiency, preferably on the order of 3 to 70% of the condensate withdrawn from the lower part of the vertical multi-tube heat exchanger. In this connection, the temperature of the condensate is, usually, approximately from 20 to 60° C.

It should be noted here that in the present invention, the solution containing polymerization inhibitor introduced into the receiving changer of the vertical multi-tube heat exchanger may not be a solution formed by circulating a part of the condensate from the lower part of the heat exchanger and may be a solution obtained by adding a polymerization inhibitor to the crude acrylic acid-containing solution from other systems.

As the polymerization inhibitor, all of the polymerization inhibitors conventionally employed for the production of (meth)acrylic acids may be used, and one member or two or more members of, for example, phenols such as hydroquinone and hydroquinone monomethyl ether, amines such as phenothiazine and diphenylamine, heavy metal salts such as copper dibutyldithiocarbamate and manganese acetate, a nitroso compound, a nitro compound, and aminoxyls such as tetramethylpiperidinoxyl derivative, may be used.

The concentration of the polymerization inhibitor in the solution containing polymerization inhibitor is preferably on the order to 10 to 2,000 ppm from the viewpoint of sufficiently obtaining the polymerization preventing effect due to the addition of a polymerization inhibitor and furthermore, preventing a problem in the post process, such as precipitation. Above all, in the present invention, based on the polymerization preventing effect attributable, as described above, to forming a liquid flow layer with a predetermined liquid depth on the upper tube plate, the concentration of the polymerization inhibitor can be set to be slightly lower than in conventional methods.

EXAMPLES

Although the present invention is described in greater detail below by referring to Examples, the present invention is not limited to the following Examples. In this connection, Examples and Comparative Examples were performed in a test facility, and the dimension of each section differs from that in the actual equipment.

For the sake of convenience of description, first, Comparative Examples are described.

Comparative Example 1

A toluene extraction solution containing 23 wt % of acrylic acid was obtained as a raw material of propylene through a reaction step of performing a catalytic gas phase oxidation reaction, a collection step of letting the acrylic acid-containing gas obtained in the reaction solution be absorbed in water to obtain an aqueous acrylic acid solution, and an extraction step of subjecting the obtained aqueous acrylic acid solution to extraction using toluene. The extraction solution was temporality stored in a drum and thereafter, fractional distillation of acrylic acid was continuously performed in the distillation column (1) illustrated in FIG. 1. The top pressure of the distillation column (1) and the reflux ratio were set to be 10 kPa and 1.2, respectively; the distillate amount was adjusted such that the amount of acrylic acid distilled out of the tope becomes 3% or less relative to the feed amount; a bottom liquid in an amount of 2% in terms of weight ratio to the amount of feed liquid was withdrawn from the bottom; and a crude acrylic acid vapor was withdrawn from the middle withdrawal line (13). The temperature inside the column was 44° C. at the top, from 94 to 95° C. in the middle withdrawal section, and from 103 to 105° C. at the bottom.

Through the middle withdrawal line (13) of which outer periphery was steam-heated, a crude acrylic acid vapor at 95 to 96° C. was fed to a vertical multi-tube heat exchanger (14).

As the vertical multi-tube heat exchanger, a heat exchanger having 19 SUS316-made heat transfer tubes with an inside diameter of 1 inch, in which upper ends of all heat transfer tubes did not protrude from the upper tube plate surface and were smoothed flush with the upper tube plate surface, was used. The cooling water feed temperature was from 31 to 33° C., and the temperature of the condensed acrylic acid was from 32 to 33° C. About 5% of the condensate was circulated to the receiving chamber side. To the circulating liquid, an acrylic acid solution of phenothiazine was added as a polymerization inhibitor such that the phenothiazine concentration becomes 100 ppm. An atomizing nozzle was provided on the tip of the circulation line in order for the circulating liquid to spread all over the upper tube plate.

When distillation was performed in this way, a strainer provided in the circulation line was clogged on the second day of operation and although it was changed to a strainer in parallel, the renewed strainer was also clogged in half a day, resulting in a shutdown of the distillation column.

After water washing, the vertical multi-tube heat exchanger was opened, as a result, about 5 L of a polymerization product in a swollen state was observed on the upper tube plate surface, on the inner wall surface of the heat transfer tube, and in the border part of the lower lid section.

Comparative Example 2

The operation was performed under the same conditions as in Comparative Example 1 except that the amount of the crude acrylic acid circulating liquid circulated to the upper tube plate surface was doubled. As a result, abrupt clogging of the strainer occurred on the third day of operation, and the operation was shut down. When the vertical multi-tube heat exchanger was opened after water washing, the amount of the polymerization product observed was about 2 L.

Comparative Example 3

Figure 3:
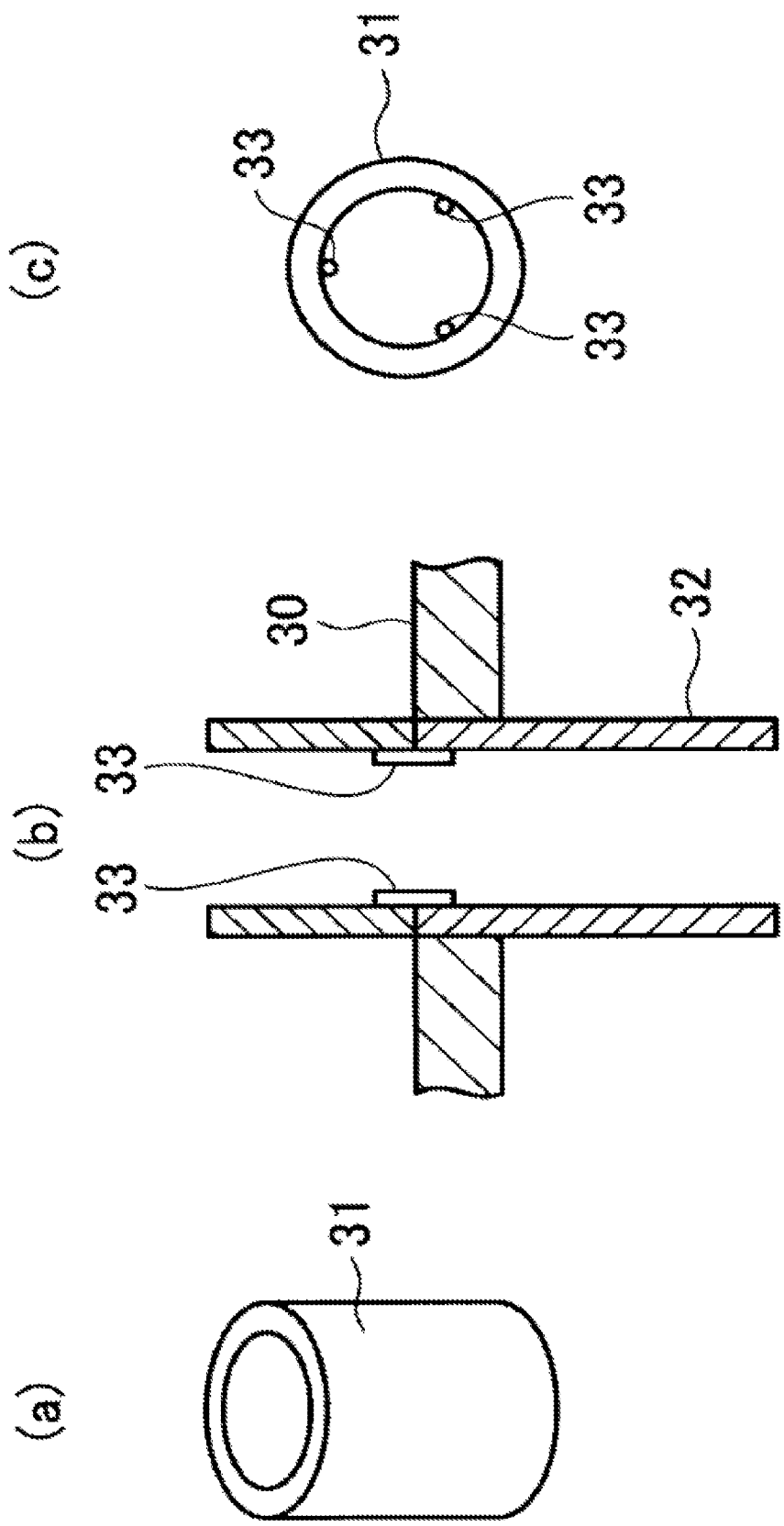
FIG. 3 is a diagram illustrating a short tube fixing structure in Comparative Example 3, wherein FIG. 3(*a*) is a perspective view of a short tube, FIG. 3(*b*) is a cross-sectional view illustrating a short tube fixing part of the upper tube plate, and FIG. 3(*c*) is a plan view of FIG. 3(*b*).

In the vertical multi-tube heat exchanger used in Comparative Example 1, a 10 mm-long short tube 31 illustrated in FIG. 3(a) having the same thickness and inside diameter as those of the heat transfer tube was used, and as illustrated in FIGS. 3(b) and (c), the short tube 31 was placed by putting its end face into contact with the end face of the heat transfer tube 32 exposed to be flush with the top surface of the upper tube plate 30 and then fixed by welding the inner wall surface of the short tube 31 and the inner wall surface of the heat transfer tube 32 with use of three wires 33 of 3 mm in diameter, thereby creating a state where upper ends of all heat transfer tubes are protruded by 10 mm from the upper tube plate surface. The materials of the short tube 31 and wires 33 all are the same SUS316 as that of the vertical multi-tube heat exchanger. In this state, the operation was performed under the same conditions as in Comparative Example 1. As a result, substantially no trapped material was observed in the strainer until the second day of operation, but on the third day, the gas from the distillation column did not flow due to clogging inside the column, resulting in an emergency stop. When the interior of the vertical multi-tube heat exchanger was checked after water washing, many polymerization products were accumulated on the upper tube plate surface, and some heat transfer tubes were completely clogged with the polymerization product.

Reference Example 1

The operation was performed under the same conditions as in Comparative Example 3 except that out of short tubes welded to heat transfer tubes, only one short tube at the center was removed. This state is a state where only one heat transfer tube at the center is a non-protruding heat transfer tube and other 18 heat transfer tubes are protruded by 10 mm. As a result, substantially no trapped material was observed in the strainer even after operation for 3 days. When the vertical multi-tube heat exchanger was checked after water washing, only a lump of the polymerization product was slightly observed at an outer circumferential part of the upper tube plate surface.

Example 2

The operation was performed for 3 days under the same conditions as in Example 1 except that out of short tubes at the positions close to the outermost circumference, three short tubes at point-symmetric positions on the upper tube plate surface were further removed. This state is a state where a total of four heat transfer tubes, i.e., one heat transfer tube at the center and three heat transfer tubes at regular interval positions in the outer circumference, are a non-protruding heat transfer tube and other 15 heat transfer tubes are protruded by 10 mm. During the operation period, a trapped material in the strainer was not observed except for a dust that is thought to get mixed in at the time of opening. A lump of the polymerization product was also not observed by checking after water washing, but when all short tubes were removed, streaks due to dirt were observed in about half of short tube junctions.

Reference Example 2

An apparatus having the same structure as in Comparative Example 1 was newly made except that as illustrated in FIG.

Figure 4:
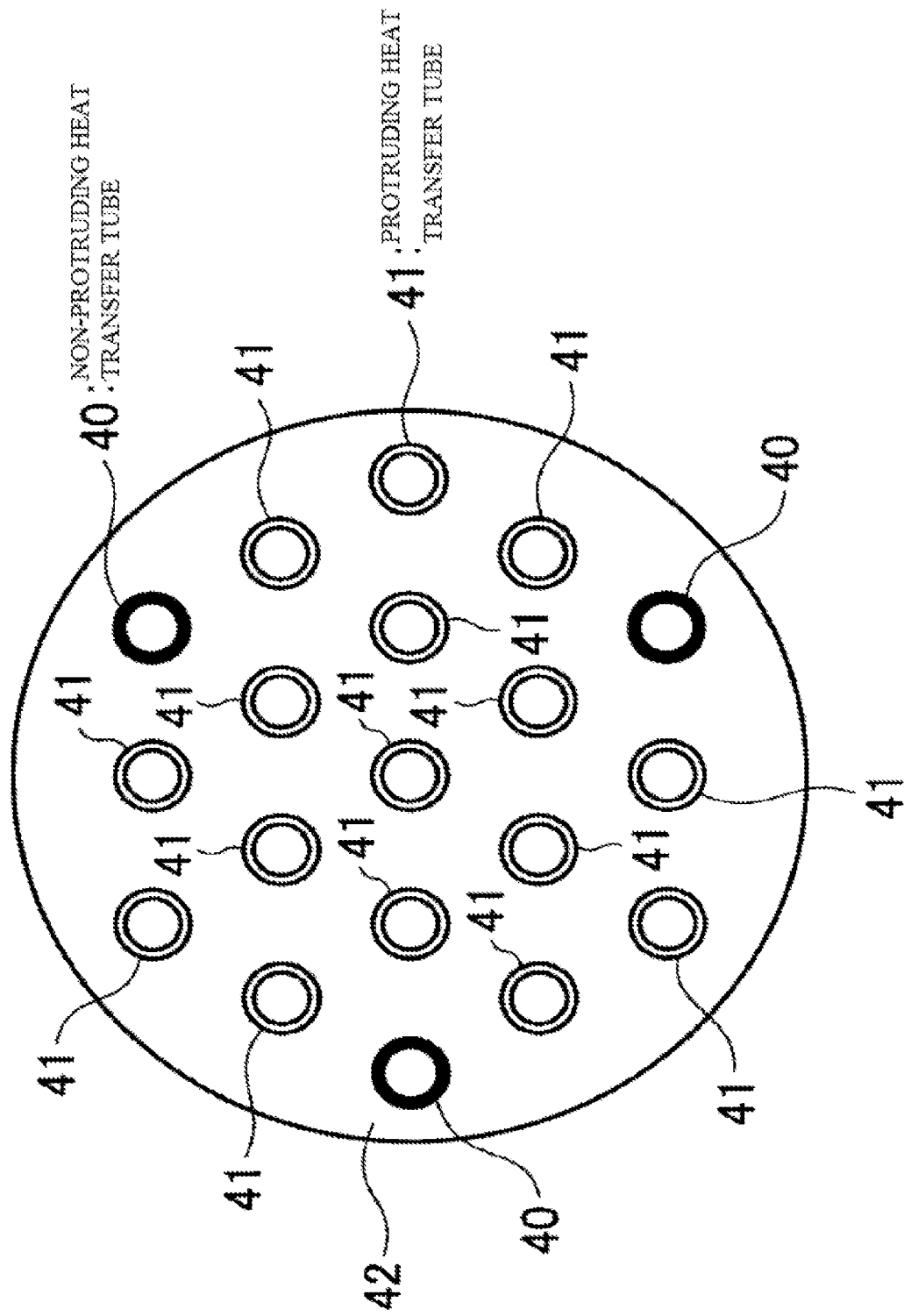
FIG. 4 is a plan view of the upper tube plate of the vertical multi-tube heat exchanger used in Example 1.

4, 16 heat transfer tubes out of 19 heat transfer tubes (inside diameter: 1 inch) provided on the upper tube plate of a vertical multi-tube heat exchanger were a protruding heat transfer tube 41 protruded by 5 mm from the top surface of the upper tube plate 42 and three non-protruding heat transfer tubes 40 were evenly provided at 3 positions in the outer circumference, and the operation was performed under the same conditions as in Comparative Example 1. In FIG. 4, in order to clearly distinguish between the protruding heat transfer tube 41 and the non-protruding heat transfer tube 40, the upper end surface of the non-protruding heat transfer tube 40 is blackened. Trapping of a polymerization product in the strainer was not recognized in the operation continued for 2 weeks and although the amount of phenothiazine fed was stepwise halved in the subsequent one week, a polymerization product was not observed as well. The operation was continued for 2 weeks by holding this state and then stopped. When the vertical multi-tube heat exchanger was opened after water washing, no polymerization product was observed other than that streaks due to a polymerization product were observed on the inner wall surface of one heat transfer tube.

The presence or absence of a liquid flow layer formed on the upper tube plate surface and the liquid depth thereof were confirmed by feeding water in the same amount as the amount of the circulating liquid in each Example in the state where the upper lid section of the vertical multi-tube heat exchanger used in Examples 1 to 3 and Comparative Examples 1 to 3 was removed, and found to be as follows.

In Comparative Examples 1 and 2 where all heat transfer tubes were a non-protruding heat transfer tube, a liquid flow layer having a depth was not formed all over the upper tube plate surface.

In Comparative Example 3 where all heat transfer tubes were a protruding heat transfer tube, the liquid depth was 10 mm or more, but because of flowing in the heat transfer tube by an overflow, only the liquid on the outermost surface flowed toward the heat transfer tube, and the liquid in the lower part of the layer did not flow, failing in forming a liquid flow layer in which the liquid flows over the entire layer.

On the other hand, in Examples 1 to 3 where only some heat transfer tubes were a non-protruding heat transfer tube but the remainings were a protruding heat transfer tube, a liquid flow layer was formed; in Example 1 where only one heat transfer tube at the center was a non-protruding heat transfer tube, the liquid depth was 4 mm or more; and in Example 2 where a total of four heat transfer tubes at the center and in the outer circumference were a non-protruding heat transfer tube and in Example 3 where three heat transfer tubes in the outer circumference were a non-protruding heat transfer tube, the liquid depth was 3 mm or more.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2016-128861) filed on Jun. 29, 2016, the contents of which are incorporated herein by way of reference.

DESCRIPTION OF REFERENCE NUMERALS AND SIGNS

1: Distillation column
2: Regular filler
3: Irregular filler
4: Plates
5: Feed line
6: Top gas line
7: Heat exchanger
8: Reflux tank
9: Reflux line
10: Circulation line
11: Reboiler
12: Withdrawal line
13: Middle withdrawal line
14: Vertical multi-tube heat exchanger
14A: Tubular body
14a, 14b: Lid section
15: Drum
16: Line to next step
17: Circulation line
18: Polymerization inhibitor feed line
19: Upper tube plate
20, 40: Non-protruding heat transfer tube
21, 41: Protruding heat transfer tube
31: Short tube
33: Wire
42: Upper tube plate

The invention claimed is:

1. A production method of a (meth)acrylic acid or an ester thereof, comprising:
   forming a distillation gas in a distillation column from a process liquid containing a (meth)acrylic acid or an ester thereof and condensing the distillation gas in a vertical multi-tube heat exchanger,
   wherein the vertical multi-tube heat exchanger comprises:
   a tubular body, an upper tube plate and a lower tube plate arranged respectively on the upper end side and the lower end side of the tubular body, a plurality of heat transfer tubes erected between the upper tube plate and the lower tube plate, and lid sections arranged respectively on the upper side of the upper tube plate and on the lower side of the lower tube plate,
   wherein
   some of the plurality of heat transfer tubes have an upper end protruding above the upper tube plate, and the remaining heat transfer tubes do not protrude above the upper tube plate,
   the number of non-protruding heat transfer tubes is 3 or more,
   the non-protruding heat transfer tubes are provided in a symmetric even arrangement on the upper tube plate surface and are located in a central part and an outer circumferential part or in a central part and near the outer circumferential part of the upper plate,
   the distillation gas introduced into a receiving chamber formed by the upper tube plate and the lid section on the upper side of the upper tube plate is cooled in the course of passing through the heat transfer tubes to form a condensate,
   a solution containing a polymerization inhibitor is introduced into the receiving chamber, and
   the solution containing the polymerization inhibitor contacts the distillation gas in the receiving chamber and flows down inside the non-protruding heat transfer tubes from the upper tube plate after forming a liquid flow layer on the upper tube plate.

2. The production method of a (meth)acrylic acid or an ester thereof according to claim 1, wherein the liquid depth of the liquid flow layer is 2 mm or more.

3. The production method of a (meth)acrylic acid or an ester thereof according to claim 1, wherein the solution containing polymerization inhibitor contains the condensate.

4. The production method of a (meth)acrylic acid or an ester thereof according to claim 1, wherein a protrusion height of the protruding heat transfer tube which is protruded above the upper tube plate is 3 mm or more.

* * * * *